United States Patent [19]

Murad

[11] Patent Number: 5,972,999
[45] Date of Patent: *Oct. 26, 1999

[54] PHARMACEUTICAL COMPOSITIONS AND METHODS FOR IMPROVING WRINKLES AND OTHER SKIN CONDITIONS

[76] Inventor: Howard Murad, 4316 Marina City Dr., Marina del Rey, Calif. 90292

[*] Notice: This patent is subject to a terminal disclaimer.

[21] Appl. No.: 09/146,554

[22] Filed: Sep. 3, 1998

Related U.S. Application Data

[63] Continuation of application No. 08/787,358, Jan. 22, 1997, Pat. No. 5,804,594.

[51] Int. Cl.⁶ .................. A61K 31/715; A61K 31/34; A61K 31/19
[52] U.S. Cl. .................. 514/474; 514/557; 514/62; 514/54; 514/801; 424/417
[58] Field of Search .................. 514/474, 557, 514/801, 62, 54; 424/417

[56] References Cited

U.S. PATENT DOCUMENTS

| | | | |
|---|---|---|---|
| 3,232,836 | 2/1966 | Carlozzi et al. | 167/65 |
| 3,697,652 | 10/1972 | Rovati et al. | 424/180 |
| 3,773,930 | 11/1973 | Mohammed et al. | 424/180 |
| 4,285,964 | 8/1981 | Niebes et al. | 424/283 |
| 4,414,202 | 11/1983 | Silvetti | 424/147 |
| 4,424,232 | 1/1984 | Parkinson | 424/279 |
| 4,486,416 | 12/1984 | Soll et al. | 424/180 |
| 4,518,614 | 5/1985 | Parkinson | 514/2 |
| 4,642,340 | 2/1987 | Senin et al. | 536/55.2 |
| 4,647,453 | 3/1987 | Meisner | 424/54 |
| 4,716,224 | 12/1987 | Sakurai et al. | 536/55.1 |
| 4,938,969 | 7/1990 | Schinitsky et al. | 484/642 |
| 4,956,173 | 9/1990 | Le Fur et al. | 424/63 |
| 5,153,174 | 10/1992 | Band et al. | 514/12 |
| 5,162,303 | 11/1992 | Goodman | 514/2 |
| 5,198,465 | 3/1993 | Dioguardi | 514/474 |
| 5,281,196 | 1/1994 | Sultenfuss | 604/20 |
| 5,296,500 | 3/1994 | Hillebrand | 514/562 |
| 5,308,627 | 5/1994 | Umbdenstock, Jr. | 424/639 |
| 5,332,579 | 7/1994 | Umbdenstock | 424/639 |
| 5,364,845 | 11/1994 | Henderson | 514/54 |
| 5,371,089 | 12/1994 | Rattan | 514/261 |
| 5,415,875 | 5/1995 | Kakoki et al. | 424/581 |
| 5,587,363 | 12/1996 | Henderson | 514/54 |

FOREIGN PATENT DOCUMENTS

| | | |
|---|---|---|
| 1181693 | 1/1985 | Canada . |
| 2066306 | 10/1992 | Canada . |
| 0 167363 A2 | 1/1986 | European Pat. Off. . |
| 4029915 | 2/1992 | Japan . |
| 896940 | 5/1962 | United Kingdom . |

OTHER PUBLICATIONS

Lubell, A., "Antioxidants, Aging and the Skin", *Cosmetic Dermatology*, 9(7):58–60 (1996).
Medline Abs., Swain, R., et al., "Vitamins As Therapy in the 1990's", *J. American Board of Family Practice*, 8(3):206–16 (1995).
Medline Abs., Todd, S., et al., "An Investigation of the relationship between antioxidant vitamin intake and coronary heart disease in men and women using logistic regression analysis", *J. Clinical Epidemiology*, 48(2):307–16 (1995).
Medline Abs., Nachbar, F., et al., "The role of Vitamin E in normal and damaged skin", *J. Molecular Medicine*, 73(1):7–17 (1995).
Medline Abs., Werman, M.J., et al., "Gender, dietary copper and carbohydrate source influence cardiac Collegen and Iysyl oxidase in weanling rats", *J. Nutrition*, 125(4):857–63 (1995).
Medline Abs., Shan, Z., et al., "Intracellular glutathione influences collagen generation by mesangial cells", *Kidney International*, 46(2):388–95 (1994).
Medline Abs., Maffei, F., et al., "Free radicals scavanging action and anti–enzyme activities of procyandines from *Vitis vinifera*. A mechanism for their capillary action", *Arzneimittal–Forschung*, 44(5):592–601 (1994).
Medline Abs., Oyama, Y., et al., "Myricetin and quercetin, the flavonoid constituents of Ginko Biloba extract greatly reduce oxidative metabolism in both resting and Ca(2+)—loaded brain neurons", *Brain Research*, 635(1–2):125–9 (1994).
Medline Abs., Asman, B., et al., "Reduction of collagen degredation in experimental granulation tissue by vitamin E and selenium", *J. Clinical Periodontology*, 21(1):45–7 (1994).
Nelder, K.H., "Nutrition and the Skin", Amer. Acad. Derm. Annl. Mtg., Dec. 6, 1993.
Medline Abs., Xie, B., et al., "Antioxident properties of fractions and polyphenol constituents from green, oolong and black teas", *Life Sciences*, 17(2):77–84 (1993).

(List continued on next page.)

*Primary Examiner*—Keith D. MacMillan
*Attorney, Agent, or Firm*—Pennie & Edmonds LLP

[57] ABSTRACT

This application relates to a pharmaceutical composition for the prevention and treatment of skin conditions in a patient having a sugar compound that is converted to a glycosaminoglycan in the patient in an amount sufficient to thicken the skin, a primary antioxidant component in an amount sufficient to substantially inhibit the formation of collagenase and elastase, at least one amino acid component in an amount sufficient to assist in the thickening of the skin, and at least one transition metal component in an amount effective to bind collagen and elastic fibers and rebuild skin. In one preferred form, the composition further includes a catechin-based preparation, a glucosamine or a pharmaceutically acceptable salt or ester thereof, and a chondroitin or a pharmaceutically acceptable salt or ester thereof. In a more preferred form, the invention further includes a vitamin E source, a cysteine source, a vitamin $B_3$ source, quercetin dihydrate, pyridoxal 5 phosphate-Co $B_6$, a methionine source, and a vitamin A source. The invention further relates to a method for the prevention or treatment of skin conditions by administering the pharmaceutical composition in an amount therapeutically effective to modify the thickness of the skin to prevent or treat at least one skin condition.

14 Claims, No Drawings

OTHER PUBLICATIONS

Medline Abs., Parto, K., et al., "Osteoporosis in lysinuric protein intolerance", *J.Inherited Metabolic Disease* 16(2):441–50 (1993).

Medline Abs., Gimenez, A., et al., "Influence on dietayr zinc on hepatic collagen and prolyl hydroxlase activities in alcoholic rats", *Hepatology*, 16(3):815–9 (1992).

Medline Abs., Reiser, K., et al., "Enzymatic and nonenzymatic cross–linking of collagen and elastin", *Faseb Journal*, 6(7):2439–49 (1992).

Bucci, L., et al., Glucosamine—A New Potent Nutraceutical for Connective Tissues, *Nutritional Supplement Advisor*, Jul. 1992.

Medline Abs., Deucher, G.P., "Antioxidant therapy in the aging process", 62:428–37 (1992).

Medline Abs., Pihlajaniemi, T., et al., "Prolyl 4–hydroxylase and its role in collagen synthesis", *J. Hepatology*, 13 Supp(3):S2–7 (1991).

Thomas, P., "Vitamin C Eyed for Topical Use as Skin Presever", *Medical World News*, Mar., 1991, p. 12.

Grevenstein, J., et al., "Cartilage Changes in Rats Induced by Papain and the Influence of Treatment With N–Acetylglucosamine", *Acta Orthopaedica Belgica*, 57(2): 157–161 (1991).

Cermele, D., et al., "Physiological Changes in Ageing Skin", *British Journal of Dermatology* (1990) I11, Supplement 35, pp. 13–20.

Medline Abs., Zafirov, D., et al., "Antiexudative and capillaritonic effects of procyanidines isolated from grape seeds (V. Vinifera)", *Acta Physiologica et Pharmacologica Bulgarica*, 16(3):50–4 (1990).

Medline Abs., Stoss, H., "Pathologic anatomy of osteogenesis imperfecta. Light and electron microsopic studies of supportive tissue and skin", *Veroffentlichungen aus der Pathologie*, 134:1–88 (1990).

Reddy, G.K., et. al., "Studies on the Metabolism of Glycosaminoglycans Under the Influence of New Herbal Anti–Inflammatory Agents", *Biochemical Pharmacology*, 38(20):3527–3534 (1989).

Fenske, N., et al., "Structural and Functional Changes of Normal Aging Skin", *Journal of the American Academy of Dermatology*, 15(4):571–585, Part 1 (1986).

Setnikar, I., et al., "Pharmacokinetics of Glucosamine in the Dog and in Man", *Arneim. Forsch/Drug Res.* 36(1):729–733, No. 4 (1986).

Kuijer, R., et al. "Influence of Constituents of Proteoglycans on Type II Collagen Fibrillogenesis", *Collagen and Related Research*, 5:379–91 (1985).

Tapadinhas, M. J., et al., "Oral Glucosamine Sulphate in the Management of Arthrosis: Report on a Multi–Centre Open Investigation in Portugal", *Pharmatherapeutica*, 3(3):157–168 91982).

D'Ambrosio, E., et al., "Glucosamine Sulphate: A Controlled Clinical Investigation in Arthrosis", *Pharmatherapeutica*, 2(8):504–508 (1981).

Drovanti, A., et al., "Therapeutic Activity of Oral Glucosamine Sulfate in Osteoarthrosis: A Placebo–Controlled Double–Blind Investigation", *Clinical Therapeutics*, 3(4):1–6 (1980).

Montagna, W., et al., "Structural Changes in Aging Human Skin", *The Journal of Investigative Dermatology*, 73(1):47–53 (1979).

Murray, M. T., "Arthritis—A Natural Solution". (1980).

PHARMACEUTICAL COMPOSITIONS AND METHODS FOR IMPROVING WRINKLES AND OTHER SKIN CONDITIONS

CROSS-REFERENCE TO RELATED APPLICATIONS

This is a continuation of application Ser. No. 08/787,358, filed Jan. 22, 1997 U.S. Pat. No. 5,804,594.

TECHNICAL FIELD

This application relates to pharmaceutical compositions, as well as methods, to supplement collagen and elastic tissues and thicken the dermis for the treatment of wrinkles and other skin conditions.

BACKGROUND OF THE INVENTION

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by the structural changes in the skin due to aging and excessive sun exposure. The physiological changes associated with skin aging include impairment of the barrier function and decreased turnover of epidermal cells, for example. [Cerimele, D., et al., *Br. J. Dermatol.,* 122 Suppl. 35, p. 13–20 (April 1990)].

The mechanical properties of the skin, such as elasticity, are controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, bumps, bruises or wrinkles, it roughens, and it has reduced ability to synthesize Vitamin D. Aged skin also becomes thinner and has a flattened dermoepidermal interface because of the alterations in collagen, elastin, and glycosaminoglycans. [Fenske, N. A, and Lober, C. W., *J. Am. Acad. Dermatol.,* 15:571–585 (Oct. 1986); Montagna, W. and Carlisle, K., *Journal of Investigative Dermatol.,* 73(1):47–53 (1979)].

A variety of vitamins and minerals have in individually been administered to treat certain skin and other problems that occur when the patient has a deficiency of that vitamin or mineral. Vitamin A, for example, assists in the treatment of acne and to facilitate wound healing; vitamin C (ascorbic acid) assists in the prevention of skin bruising and wound healing; vitamin E is an antioxidant; and copper assists in the treatment of elastic tissue defects. [Neldner, K. H., *Amer. Acad. Derm. Annl. Mtg.,* Wash. D.C., Dec. 6, 1993]. Topical use of vitamin C is also believed to ward off sun damage, reduce breakdown of connective tissues, and possibly promote collagen synthesis. [Dial, W., *Medical World News,* p. 12, March 1991]. Vitamin E is used topically as an anti-inflammatory agent, for enhancement of skin moisturization, for UV-ray protection of cells, and for retardation of premature skin aging.

Catechin-based preparations, including proanthanols and proanthocyanidins are powerful antioxidants. These compounds are found in flowers, plant leaves, and grape seeds, for example. [Lubell, A., *Cosmetic Dermatol.,* 9(7):58 & 60 (July 1996)].

N-Acetylglucosamine and glucosamine have been examined for use in the prevention and treatment of degenerative joint diseases and cartilage loss, and found to increase the glycosaminoglycans present in the cartilage to restore cartilage. [See Grevenstein, J., et al., *Acta Orthopaedia Belgica,* 57(2):157–161 (1991); Setnikar, I., *Drug Res.,* 36(4):720–733 (1986); Drovanti, A., et al, *Clin. Therap.,* 3(4):1–6 (1980)]. Glucosamine has also been examined in connection with arthritis [See, e.g., Murray, M. T.] and oral and injected glucosamine have been reported to be useful for arthrosic patients. [Tapadinhas, M. J., et al., *Pharmatherapeutica,* 3(3):157–168 (1982); D'Ambrosio, E., et al., *Pharmatherapeutica,* 2(8):504–508 (1981)].

The metabolism of glycosaminoglycans under the influence of herbal and other anti-inflammatory agents has been examined by measuring glycosaminoglycans in the skin, liver, kidney, and spleen after administration of several compounds. [Reddy, G. K., et al., *Biochem. Pharmacology,* 38(20) :3527–3534 (1989)].

In addition to their individual use to supplement a deficiency in a patient, various of the above ingredients have been combined to form pharmaceuticals designed to prevent and treat certain cellular, skin, and other conditions. For example, U.S. Pat. No. 3,773,930 discloses a low residue, dietary composition having at least one amino acid and a quantity of non-amino acid derived caloric material sufficient to obviate the diarrhea problem of straight amino acid compositions. A flavoring material may also be included to render the composition more palatable.

U.S. Pat. No. 4,285,964 discloses a salt of (+)-catechin formed by reacting (+)-catechin with at least a basic amino acid, such as L-lysine and L-arginine; and a hydrosoluble double salt formed from the reaction product of (+)-catechin with a basic amino-acid, such as L-lysine and L-arginine, and another inorganic or organic acid. The patent further discloses methods of treating degenerative diseases of the connective tissue by topically administering the composition.

U.S. Pat. No. 4,414,202 discloses a composition for the treatment of skin wounds with a buffered salt solution having a pH between 6 to 7.8 and administering a starch hydrolysate compound, and preferably including alphaketoglutaric acid or alphaketoglutarate salts. Optional additives to the composition include ascorbic acid or salts thereof, ferrous salts, and glycine, L-Proline, and L-Lysine.

U.S. Pat. No. 4,424,232 discloses a topical composition for the treatment of herpes simplex, cold sores, lesions, and other painful skin conditions including L-lysine, gibberellic acid, and urea in an inert carrier having water. The composition may also include L-ascorbic acid, as well as methyl paraben, propyl paraben, or mixtures thereof.

U.S. Pat. No. 4,647,453 discloses a method and composition for treatment of tissue degenerative inflammatory disease in animals and humans by oral administration of ascorbic acid, bioavailable calcium, a precursor or stimulant of epinephrine or nor-epinephrine of tyrosine or phenylalanine, and an anti-inflammatory substance selected from anti-inflammatory sugars, amino sugars and biocompatible acid addition salts thereof, and anti-inflammatory amino acids, to promote connective tissue regrowth.

U.S. Pat. No. 5,198,465 discloses a composition for treating precursor deficiencies in the synthesis of collagen with proline, glycine, lysine, vitamin C, and one or more compounds selected from α-ketoglutaric acid, methionine, cysteine, cystine, valine, and pharmaceutically acceptable diluents and excipients.

U.S. Pat. Nos. 5,332,579 and 5,308,627 disclose a nutritional supplement to assist persons recovering from addiction by administering a variety of vitamins and minerals including enzyme activating substances such as magnesium and zinc; an enzyme co-factor that is a vitamin like various vitamin B complexes; an enzyme producer such as an amino acid like glutamic acid; an herbal antispasmodic substance like Valerian root; and vitamin C.

U.S. Pat. No. 5,415,875 discloses a method of suppressing formation of lipid peroxide and removing peroxide by applying to the skin a decomposed product of shell membrane and tocopherol and derivatives. Lysine, proline, Vitamin C, for examples, are listed among a vast genus of optional additives.

The above references, however, do not teach pharmaceutical compositions or methods for improving skin wrinkles along with other conditions, such as skin elasticity and softness. Thus, it is desired to find a pharmaceutical composition and a method for the prevention and treatment of wrinkles and other skin conditions. The present invention advantageously provides pharmaceutical compositions, as well as methods of treatment comprising the administration of such compositions, to repair skin for the prevention and treatment of wrinkles and other skin disorders.

SUMMARY OF THE INVENTION

The present invention relates to a pharmaceutical composition for the prevention and treatment of skin conditions in a patient having a sugar compound that is converted to a glycosaminoglycan in the patient in an amount sufficient to thicken the skin, a primary antioxidant component in an amount sufficient to substantially inhibit the activity of collagenase and elastase, at least one amino acid component in an amount sufficient to assist in the thickening of the skin, and at least one transition metal component in an amount effective to bind collagen and elastic fibers and rebuild skin.

In one embodiment, the sugar compound is present in about 5 to 50 weight percent, the primary antioxidant component is present in about 5 to 50 weight percent, the amino acid component is present in about 8 to 60 weight percent, and the transition metal component is present in about 0.5 to 15 weight percent of the composition. In another embodiment, the sugar compound includes an N-acetylglucosamine compound or salt or ester thereof, the primary antioxidant component includes an ascorbic acid component or salt or ester thereof, at least two amino acids selected from the group of proline, lysine, cysteine, and methionine are present, and at least two the transition metal components including zinc, manganese or copper, or mixtures thereof, are present. In yet another embodiment, the composition further includes a pharmaceutically acceptable carrier or excipient.

In a more preferred embodiment, at least three transition metal components are present, one of which is zinc monomethionine, one of which is manganese ascorbate, and one of which is copper sebacate, wherein the zinc is present in about 10 to 30 weight percent of the complex and the manganese is present in about 5 to 20 weight percent of the complex, and the copper is present in about 5 to 20 weight percent of the complex. In another preferred embodiment, the N-acetylglucosamine is present in about 5 to 30 weight percent, the ascorbic acid is present in about 5 to 50 weight percent, the amino acid comprises lysine and proline, wherein each is present in about 4 to 25 weight percent, and the zinc monomethionine and the manganese ascorbate are each present in about 1 to 10 weight percent and the copper sebacate is present in about 0.1 to 5 weight percent of the composition.

In one preferred embodiment of the invention, the composition further includes a catechin-based preparation, a glucosamine or a pharmaceutically acceptable salt or ester thereof, and a chondroitin or a pharmaceutically acceptable salt or ester thereof. In a more preferred embodiment, the catechin-based preparation is a proanthanol or proanthocyanidin, and the glucosamine and chondroitin are each a sulfate or succinate. In a most preferred embodiment, the proanthocyanidin is grape seed extract present in about 0.5 to 5 weight percent, the glucosamine is D-glucosamine sulfate present in about 3 to 17 weight percent, wherein the glucosamine is about 60 to 90 weight percent of the salt, and the chondroitin is chondroitin sulfate present in about 3 to 17 weight percent of the composition, wherein the chondroitin is preferably present as about 65 to 95 weight percent of the salt.

In another preferred embodiment, the composition further includes a vitamin E source, a cysteine source, a vitamin $B_3$ source, quercetin dihydrate, pyridoxal 5 phosphate-Co $B_6$, a methionine source, and a vitamin A source. In a more preferred embodiment, the vitamin E is D-alpha tocopheryl acid succinate present in about 1 to 15 weight percent, the vitamin $B_3$ is niacinamide present in about 0.5 to 15 weight percent, the vitamin A is vitamin A palmitate present in about 0.1 to 5 weight percent, the cysteine is N-acetyl cysteine present in about 1 to 10 weight percent, the methionine is preferably L-selenomethionine present in about 0.1 to 5 weight percent, the quercetin dihydrate is present in about 0.5 to 15 weight percent, and the pyridoxal 5 phosphate-Co $B_6$ is present in about 0.1 to 5 weight percent of the composition.

The invention further relates to a method for the prevention or treatment of skin conditions, wherein the skin has a thickness of dermis and collagen, which includes administering the pharmaceutical composition above in an amount therapeutically effective to modify the thickness of the skin to prevent or treat at least one skin condition.

In one embodiment according to the invention, the skin condition treated is at least one of wrinkles, fine lines, thinning, reduced skin elasticity, reduced skin moisture, spider veins, senile purpura, sun damaged skin, aging skin, or rough skin. In another embodiment, the composition is administered orally. In a preferred embodiment, the composition is administered as a tablet or capsule having about 1 mg to 2,000 mg of composition. In a more preferred embodiment, the tablet or capsule has about 200 mg to 1,600 mg of composition, and in a most preferred embodiment, the tablet or capsule has about 600 mg to 1,000 mg of composition.

In another embodiment, the composition is administered in conjunction with concurrent or subsequent treatment by at least one additional pharmaceutical composition for the prevention or treatment of a skin condition.

The ranges of the components of the pharmaceutical composition may vary, but the active ingredients should be understood to add to 100 weight percent of the active pharmaceutical composition.

DETAILED DESCRIPTION OF THE PREFERRED EMBODIMENTS

A formulation for the reduction of wrinkles and the improvement of other skin conditions, such as increased skin elasticity and skin softness, has now been discovered. Moreover, the prevention or treatment of unhealthy skin, such as aged skin or skin overexposed to sunlight, may advantageously be accomplished by the administration of the pharmaceutical composition of the present invention to a human in need of treatment. The pharmaceutical composition includes the combination of a number of different components which interact to provide the desired improvements to the skin.

The advantageous pharmaceutical composition of the present invention prevents and improves skin conditions by using a sufficient amount of at least one sugar compound which is converted into glycosaminoglycans in the bloodstream, in combination with other ingredients disclosed herein to assist in thickening the dermis and supplementing collagen and elastic tissues. A thicker dermis desirably reduces the wrinkling and lines that occur when areas of the skin become thin. Various amino acids such as lysine, proline and cysteine assist in the thickening of the dermis, supplementing of collagen and elastic tissues and, consequently, reduction of wrinkles and other skin conditions. Additionally, antioxidants, such as vitamin C, inhibit collagenase and elastase, enzymes that break down collagen and elastic tissues. These antioxidants assist in the prevention of additional wrinkles and facilitate the healing of skin tissues. Finally, transition metal components are included to bind collagen fibers and inhibit elastase, an enzyme that also breaks down collagen and elastic tissue.

The composition preferably contains at least one sugar compound, and more preferably just one sugar compound, present in about 5 to 50 weight percent, preferably about 10 to 40 weight percent, and more preferably about 15 to 30 weight percent of the composition. The primary antioxidant component is preferably present in an amount of about 5 to 50 weight percent, more preferably about 10 to 40 weight percent, and most preferably about 15 to 30 weight percent of the composition. The amino acid component is preferably present in about 8 to 60 weight percent, more preferably about 15 to 50 weight percent, most preferably about 20 to 40 weight percent of the composition. The transition metal component is preferably present in about 0.5 to 15 weight percent, more preferably present in about 2 to 12 weight percent, and most preferably present in about 5 to 10 weight percent of the composition.

The first component of the composition is any sugar compound that is converted to glycosaminoglycans in the human bloodstream. Typically, this would be an N-acetylglucosamine compound, or a pharmaceutically acceptable salt or ester thereof. The N-acetylglucosamine component may be N-acetylglucosamine or any pharmaceutically acceptable salt or ester thereof, but more preferably is the N-acetylglucosamine only. This component must be present in sufficient quantity in the pharmaceutical composition to promote thickening of the dermis. The N-acetylglucosamine is present in about 5 to 30 weight percent, preferably 8 to 27 weight percent, and more preferably 12 to 24 weight percent of the pharmaceutical composition. A unit dose of N-acetylglucosamine is typically about 40 mg to 250 mg, preferably about 60 to 200, and more preferably about 100 mg to 200 mg.

The pharmaceutical composition includes a primary antioxidant, which typically is a vitamin C source and preferably is ascorbic acid, or a pharmaceutically acceptable salt or ester thereof, and more preferably is ascorbyl palmitate, dipalmitate L-ascorbate, sodium L-ascorbate-2-sulfate, or an ascorbic salt, such as sodium, potassium, or calcium ascorbate, or mixtures thereof. When oral formulations of the pharmaceutical composition are used, it is preferred that a non-acidic form of vitamin C be used to reduce the stomach irritation that may occur when using an acidic form. The vitamin C source is present in the pharmaceutical composition in about 5 to 50 weight percent, preferably about 7 to 40 weight percent, and more preferably about 10 to 25 weight percent. A unit dose of this primary vitamin C source is typically about 40 mg to 400 mg, preferably about 60 mg to 300 mg, and more preferably about 80 to 150 mg. Vitamin C is also approved by the FDA and has wide consumer acceptance, so that it can be used in amounts as high as 10,000 mg, if desired.

The pharmaceutical composition also includes at least one amino acid to assist in thickening the skin. Preferably two or more amino acids are used in combination. Either the L- or D- forms of amino acids are acceptable. Lysine and proline are the most preferred amino acids and are advantageously used in combination. Cysteine, methionine or other amino acids can also be used, if desired. The amino acids may be included in a soluble form such as the hydrochloride, i.e., L-Lysine hydrochloride. The amino acids are present in an amount of about 2 to 25 weight percent each, preferably about 4 to 20 weight percent each, and more preferably about 6 to 15 weight percent each. A unit dose for each amino acid is typically about 35 mg to 200 mg each, preferably about 50 mg to 150 mg each, and more preferably about 70 mg to 120 mg in the pharmaceutical composition. Additional useful forms of amino acid include the following: a cysteine source, preferably N-acetyl cysteine, can be present in an amount of about 1 to 10 weight percent, preferably about 2 to 8 weight percent, and more preferably about 3 to 6 weight percent of the pharmaceutical composition. A methionine source, preferably L-selenomethionine, can be present in an amount of about 0.1 to 5 weight percent, preferably 0.2 to 3 weight percent, and more preferably 0.3 to 1 weight percent of the composition, wherein the selenium component is between about 0.1 to 3 weight percent of the methionine source.

One or more transition metal compounds are included in an amount effective to bind collagen and elastic tissue to rebuild the skin. Certain transition metal compounds inhibit the elastase enzyme to inhibit collagen and elastic tissue breakdown. Preferred transition metals include zinc, manganese and copper, with combinations thereof being most preferred.

A zinc component can be added to assist in binding collagen and elastic fibers, which both assists in the prevention of wrinkles and the rebuilding of wrinkled skin. The zinc component may be any zinc compound or pharmaceutically acceptable salt thereof, but more preferably is a zinc complexed with an amino acid, and most preferably is zinc monomethionine, wherein the zinc is typically present in about 10 to 30 weight percent of the complex. The zinc component is present in about 1 to 10 weight percent, more preferably about 2 to 7 weight percent, and most preferably about 3 to 5 weight percent of the pharmaceutical composition.

A manganese component can also be added to assist in binding collagen and elastic fibers. The manganese component may be any manganese compound or pharmaceutically acceptable salt thereof, but more preferably is a manganese component which is at least partially complexed with a vitamin C source, and most preferably is manganese ascorbate or manganese ascorbic acid, wherein the manganese is typically present in about 5 to 20 weight percent of the complex. When complexed with vitamin C, this vitamin C source may be included in the overall percentage of vitamin C in the pharmaceutical composition. The manganese component is present in about 1 to 10 weight percent, more preferably about 2 to 7 weight percent, and most preferably about 2.5 to 4 weight percent of the pharmaceutical composition.

A copper component is preferably also included in the pharmaceutical composition, and may be any copper compound or pharmaceutically acceptable salt thereof, but preferably is copper sebacate, wherein the copper is typically present in about 5 to 20 weight percent of the copper sebacate. The copper component also inhibits elastase and is present in about 0.1 to 5 weight percent, preferably about 0.2 to 3 weight percent, and more preferably about 0.3 to 1 weight percent of the pharmaceutical composition. A unit dose of the pharmaceutical composition may include about 1 mg to 40 mg, preferably about 2 mg to 25 mg, and more preferably about 2.5 mg to 10 mg.

In a preferred form of the invention, the pharmaceutical composition further includes a catechin-based preparation, such as a proanthanol or proanthocyanidin, along with glucosamine or a pharmaceutically acceptable salt or ester thereof, and chondroitin or a pharmaceutically acceptable salt or ester thereof.

The catechin-based preparation, similar to vitamin C, inhibits elastase and collagenase, which is another enzyme that attacks elastic tissue and collagen. The catechin-based preparation is preferably a proanthanol or proanthocyanidin, more preferably a proanthocyanidin, and most preferably grape seed extract. These compounds are considered to be secondary antioxidants, because they are present in lesser amounts than the primary antioxidant. The catechin-based preparation is present in about 0.5 to 5 weight percent, more preferably about 0.6 to 3 weight percent, and most preferably about 0.7 to 2 weight percent of the pharmaceutical composition.

The glucosamine or a pharmaceutically acceptable salt or ester thereof, and the chondroitin or a pharmaceutically acceptable salt or ester thereof are each present in about 3 to 17 weight percent, preferably about 4 to 12 weight percent each, and more preferably about 5 to 8 weight percent each of the pharmaceutical composition. The glucosamine component preferably is present as a sulfate or succinate, and more preferably is D-glucosamine sulfate, wherein the glucosamine is preferably present as about 60 to 90 weight percent of the salt. The glucosamine content of this component contributes to the formation of glycosoaminoglycans in the skin. The chondroitin component preferably is present as a sulfate or succinate, and more preferably is chondroitin sulfate, wherein the chondroitin is preferably present as about 65 to 95 weight percent of the salt.

In a more preferred form, several optional additives are included in the pharmaceutical composition, such as a vitamin E source, a vitamin $B_3$ source, quercetin powder, pyridoxal 5 phosphate-Co $B_6$, and a vitamin A source. The vitamin E preferably is a sulfate or succinate vitamin E complex, and more preferably is D-alpha tocopheryl acid succinate. The vitamin E source is present in about 1 to 15 weight percent, preferably about 2 to 12 weight percent, and more preferably about 3 to 10 weight percent of the composition. In any event, no more than 1,500 IU should be ingested per day, as Vitamin E becomes toxic at higher doses. The vitamin $B_3$ source preferably is niacinamide, and the source is present in about 0.5 to 15 weight percent, preferably about 1 to 12 weight percent, and more preferably about 1.5 to 10 weight percent of the composition. The vitamin A source preferably is vitamin A palmitate, and the source is present in about 0.1 to 5 weight percent, preferably 0.2 to 3 weight percent, and more preferably 0.3 to 1 weight percent of the composition. In the more preferred form, the amount of vitamin A dosage is about 500,000 IU/gram per unit dose. Vitamin A is toxic at high levels, such that no more than 400,000 IU should be cumulatively ingested per day for greater than six months.

The quercetin powder is quercetin dihydrate, which is typically present in about 0.5 to 15 weight percent, preferably about 1 to 12 weight percent, and more preferably about 1.5 to 10 weight percent of the composition. The pyridoxal 5 phosphate-Co $B_6$, also known as P-5-P monohydrate, is typically present in about 0.1 to 5 weight percent, preferably 0.2 to 3 weight percent, and more preferably 0.3 to 1 weight percent of the composition.

The phrase "therapeutically effective amount" means that amount of the pharmaceutical composition that provides a therapeutic benefit in the treatment, prevention, or management of skin wrinkles and other skin conditions.

The magnitude of a prophylactic or therapeutic dose of the composition in the acute or chronic management of wrinkles will vary with the severity of the condition to be treated and the route of administration. The dose, and perhaps the dose frequency, will also vary according to the age, body weight, and response of the individual patient. In general, the total daily dose range, for the conditions described herein, is from about 10 mg to about 20,000 mg administered in single or divided doses orally, topically, transdermally, or locally by inhalation. For example, a preferred oral daily dose range should be from about 10 mg to 20,000 mg, more preferably about 2,000 mg to 16,000 mg, and most preferably about 6,000 mg to 10,000 mg of the active components (i.e., excluding excipients and carriers).

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The term "unit dose" is meant to describe a single dose, although a unit dose may be divided, if desired. About 1 to 10 unit doses of the present invention are typically administered per day, preferably about 2 to 6 doses per day, and more preferably about 4 doses per day.

Although any suitable route of administration may be employed for providing the patient with an effective dosage of the composition according to the methods of the present invention, oral administration is preferred. Suitable routes include, for example, oral, rectal, parenteral, intravenous, topical, transdermal, subcutaneous, intramuscular, and like forms of administration may be employed. Suitable dosage forms include tablets, troches, dispersions, suspensions, solutions, capsules, patches, suppositories, and the like, although oral dosage forms are preferred.

The pharmaceutical compositions used in the methods of the present invention include the active ingredients described above, and may also contain pharmaceutically acceptable carriers, excipients and the like, and optionally, other therapeutic ingredients.

The term "pharmaceutically acceptable salt" refers to a salt prepared from pharmaceutically acceptable non-toxic acids or bases including inorganic or organic acids.

Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

The compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each unit dose, i.e., tablet, cachet or capsule, contains from about 1 mg to 2,000 mg of the active ingredient, preferably about 200 mg to 1,600 mg, and more preferably about 600 mg to 1,000 mg of the composition.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1

Capsules

A large number of unit capsules are prepared by filling standard two-piece hard gelatin capsules each with the desired amount of powdered active ingredient as described above, 150 milligrams of lactose, 50 milligrams of cellulose, and 6 milligrams magnesium stearate.

Example 2

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing the desired amount of the active ingredient. The capsules are washed and dried for packaging.

Example 3

Tablets

A large number of tablets were prepared by conventional procedures so that the dosage unit included: the desired amount of active ingredient as described herein, 50 milligrams of red beet root powder, 12 milligrams of stearic acid, 10.95 milligrams of sorbitol, 3 milligrams of acdisol, 1 milligram of magnesium stearate, and 1 milligram of syloid. Appropriate coatings may be applied to increase palatability or delay absorption. A specific therapeutic formulation of the pharmaceutical composition described herein is set forth in the table below:

| Ingredient | Weight Percent (% w/w) | Amount (mg) | Chemical or Scientific Name (if different) |
| --- | --- | --- | --- |
| N-Acetylglucosamine | 17.1 | 140 | N-Acetyl D-Glucosamine |
| Vitamin C (81.2% Ascorbic Acid) | 15 | 123.2 | |
| L-Lysine (80%) | 12.2 | 100 | L-Lysine hydrochloride |
| L-Proline | 11 | 90 | |
| D-Glucosamine Sulfate (75%) | 6.5 | 53.3 | |
| Chondroitin Sulfate (80%) | 6.1 | 50 | |
| Vitamin E Succinate | 4.3 | 39.7 | D-α tocopheryl acid succinate |
| Zinc monomethionine (20%) | 3.7 | 30 | Zinc DL-methionine |
| N-Acetyl Cysteine | 3.7 | 30 | |
| Manganese Ascorbate (13% Mn) | 2.8 | 23.1 | |
| Vitamin $B_3$ Niacinamide | 2.4 | 20 | Niacinamide |

-continued

| Ingredient | Weight Percent (% w/w) | Amount (mg) | Chemical or Scientific Name (if different) |
|---|---|---|---|
| Quercetin Powder | 2.4 | 20 | Quercetin dihydrate |
| Grape Seed Extract | 0.9 | 7.5 | Proanthocyanidin |
| Pyridoxal 5 Phosphate-Co $B_6$ | 0.6 | 5 | P-5-P monohydrate |
| Selenomethionine (0.5%) | 0.5 | 4 | L-selenomethionine |
| Vitamin A Palmitate (500,000 IU/GR) | 0.5 | 4 | |
| Copper Sebacate (14%) | 0.4 | 2.9 | |
| Red beet root powder | 6.1 | 50 | Beta vulgaris rubra |
| Stearic acid | 1.5 | 12 | |
| Sorbitol | 1.3 | 11 | |
| Acdisol | 0.4 | 3 | Microcrystalline cellulose |
| Coconut oil | 0.1 | 1 | Magnesium stearate |
| Syloid | 0.1 | 1 | Silicon dioxide (amorphous) |
| Total | 820.7 | 100 | |

These tablets are an example of a preferred embodiment of a unit dose according to the present invention.

Examples 4–7

TESTING OF THE PRODUCT

The tablets of Example 3 were administered to test 73 female subjects to determine the effects on the elasticity, firmness, and presence of fine lines and wrinkles of the skin. A seven day conditioning period was used prior to initiation of the study, where subjects were instructed to discontinue use of all moisturizing products, sunscreens and liquid make-ups, and to avoid excessive UV exposure and tanning salons. Subjects were permitted to use their current eye, powder blush, and lip products, and non-moisturizing soap.

Test subjects not in the control group, which consumed placebo tablets, consumed two (2) tablets of the test material of Example 3 daily with meals. Before, and after two (2) and five (5) weeks of tablet use, the subjects were measured as described below. Before measurements were taken, all subjects were allowed to equilibrate for thirty minutes at approximately 68° F. and 44 percent relative humidity. At each measurement phase, three Corneometer readings, a negative impression using Silflo replicating material, and three Ballistometer and Cutometer readings were made on the test sites indicated below.

A total of 65 subjects completed the study, as 7 discontinued the study for unrelated reasons and 1 developed a rash for 5 days. There were 12 subjects in the control group and 53 using the tablets.

Example 4

Image Analysis

The texture of the skin, fine lines, and wrinkles were assessed by taking Silflo replicas of the periorbital area (crow's feet) at each of the three test times. These negative impressions, or Silflo replicas, were illuminated at a precisely defined angle of 35° to create shadows for analysis by shades of gray. The skin topography is defined by the: (a) number of wrinkles; (b) total area of wrinkles; (c) total length of wrinkles; (d) mean length of wrinkles; and (e) mean depth of wrinkles. The type of wrinkles was determined on the basis of depth, length, and area.

As indicated in Table I below, the number of wrinkles were significantly reduced by 34 percent ($p<0.01$) and the number of fine lines by 34 percent ($p<0.06$) as a result of 5 weeks using the test material.

TABLE I

| | Number of Wrinkles and Fine Lines | | | | | | | |
|---|---|---|---|---|---|---|---|---|
| | Number of Wrinkles | | | | Number of Fine Lines | | | |
| | Mid-Baseline | | Final-Baseline | | Mid-Baseline | | Final-Baseline | |
| | Control | Treated | Control | Treated | Control | Treated | Control | Treated |
| Average | −3 | −7 | −3 | −15 | −5 | −4 | −6 | −12 |
| Standard Deviation | 9 | 13 | 13 | 12 | 6 | 10 | 14 | 10 |
| p value | p <0.41 | | p <0.01 | | p <0.96 | | p <0.06 | |
| % Difference from Baseline | −11% | −19% | −6% | −40% | −14% | −24% | −9% | −43% |
| Total % Difference (T − C) | −8% | | −34% | | −10% | | −34% | |

T = Treated
C = Control

Example 4 indicates that use of tablets prepared by the formulation of the invention herein result in a 10 percent decrease in appearance of wrinkles and an 8 percent decrease in fine lines after only 2 weeks of treatment, and a decrease of 34 percent in both wrinkles and fine lines after 5 weeks. Additionally, the observed degree of improvement is a function of the length of treatment as indicated above. This strongly suggests the treatment has imparted an improved skin infrastructure by beneficially affecting the dermis of the skin.

Example 5

Ballistometer

The Ballistometer is an instrument designed to evaluate in vivo, in a non-invasive manner, the viscoelastic properties of the skin. It analyzes the bounce pattern displayed by a probe that is allowed to impact on the skin. The kinetic energy of the probe striking the skin is stored by the elastic components of the skin and released back to make the probe rebound to a lower height. The height to which the probe will rebound depends upon the amount of stored energy lost in shear viscosity within the skin.

The capacity of the skin to absorb mechanical energy may thus be measured. Although it is unclear exactly which layer, or layers, of the skin are responsible, the mechanical properties of the dermis/epidermis layers are controlled by the density and geometry of the network of collagen fibers. It is believed the Ballistometer describes mostly the tissues underlying the stratum corneum.

Tests were conducted with the Ballistometer on one randomly chosen side of the face, slightly below the cheek bone area. The height of first rebound and the coefficient of restitution ("COR") were measured. The COR is the ratio of the first to the second rebound. Table II, below, indicates that the COR decreases by 10 percent ($p<0.11$) and the height of the first rebound reduced by 18 percent ($p<0.02$) as a result of 5 weeks use of the product. This indicates that less of the energy of the striking probe was restored, thus, a greater amount of energy was dissipated in the skin. This suggests the skin became softer and more yielding during the test period.

small aperture (2 mm) of a probe and the depth of penetration of the skin into the probe optically with an accuracy of 0.01 mm. The probe is attached to a computer, which completely controls probe operation and plots skin deformation as a function of time. From this curve, a number of variables can be extrapolated to estimate the elastic, viscoelastic, and purely viscous behavior of the skin.

The following parameters were recorded: (a) the immediate distension ($U_e$) measured at 0.1 seconds; (b) the delayed distension ($U_v$); (c) the final distension ($U_f$), measured at 10 seconds; and (d) immediate retraction ($U_r$). The deformation parameters are extrinsic parameters dependent on skin thickness, and a variety of biologically important ratios were calculated: (a) $U_r/U_f$, a measure of net elasticity of the skin; (b) $U_r/U_e$, the biological elasticity, or measurement of the ability of the skin to regain its initial configuration after deformation; and (c) $U_v/U_e$, the viscoelastic to elastic ratio, where an increase in this ratio indicates and increase in the viscoelastic portion of the deformation and/or a relative decrease of the elastic portion.

Tests were conducted using a Cutometer on both sides of the face on the cheek area. Table III, below, indicates that the

TABLE II

| | Ballistometer Readings | | | | | | | |
|---|---|---|---|---|---|---|---|---|
| | Height of First Rebound (mm) | | | | Coefficient of Restitution | | | |
| | Mid-Baseline | | Final-Baseline | | Mid-Baseline | | Final-Baseline | |
| | Control | Treated | Control | Treated | Control | Treated | Control | Treated |
| Average | −0.16 | −0.06 | 0.49 | 0.06 | −0.02 | 0.00 | 0.01 | 0.00 |
| Standard Deviation | 0.41 | 0.48 | 0.52 | 0.51 | 0.03 | 0.02 | 0.03 | 0.03 |
| p value | $p<0.56$ | | $p<0.02$ | | $p<0.06$ | | $p<0.11$ | |
| % Difference from Baseline | −6% | 0% | 22% | 4% | −12% | −0% | 12% | 2% |
| Total % Difference (T − C) | 6% | | −18% | | 12% | | −10% | |

T = Treated
C = Control

Example 6

Cutometer

The Cutometer is a commercially available instrument (Courage & Khazaka, Germany) designed to measure the mechanical properties of the skin in a non-invasive manner. It measures the vertical deformation of the skin's surface when pulled by vacuum suction (500 mm Hg) through the delayed distension ($U_v$) decreased a significant 16 percent ($p<0.04$) after 5 weeks of treatment. This parameter reflects viscoelastic properties of the skin and, thus, the behavior of the dermis. After 5 weeks, there were no statistically significant changes in $U_e$, the immediate distension, which is primarily affected by the moisture content and mechanical properties of the stratum corneum.

TABLE III

| | Cutometer Readings | | | | | | | |
|---|---|---|---|---|---|---|---|---|
| | $U_f$ (mm) | | | | $U_e$ (mm) | | | |
| | Mid-Baseline | | Final-Baseline | | Mid-Baseline | | Final-Baseline | |
| | Control | Treated | Control | Treated | Control | Treated | Control | Treated |
| Average | 0.071 | 0.040 | 0.026 | 0.020 | 0.046 | 0.021 | 0.008 | 0.009 |
| Standard Deviation | 0.038 | 0.058 | 0.058 | 0.049 | 0.028 | 0.042 | 0.048 | 0.043 |
| p value | $p<0.11$ | | $p<0.71$ | | $p<0.08$ | | $p<0.96$ | |
| % Difference from Baseline | 39% | 20% | 16% | 11% | 36% | 16% | 11% | 10% |
| Total % Difference (T − C) | −19% | | −5% | | −20% | | −1% | |

TABLE III-continued

Cutometer Readings

| | $U_v$ (mm) | | | | $U_r$ (mm) | | | |
|---|---|---|---|---|---|---|---|---|
| | Mid-Baseline | | Final-Baseline | | Mid-Baseline | | Final-Baseline | |
| | Control | Treated | Control | Treated | Control | Treated | Control | Treated |
| Average | 0.026 | 0.020 | 0.018 | 0.010 | 0.033 | 0.017 | 0.013 | 0.008 |
| Standard Deviation | 0.015 | 0.018 | 0.015 | 0.011 | 0.018 | 0.027 | 0.030 | 0.023 |
| p value | p <0.27 | | p <0.04 | | p <0.09 | | p <0.55 | |
| % Difference from Baseline | 51% | 39% | 34% | 19% | 48% | 26% | 19% | 15% |
| Total % Difference (T − C) | −12% | | −16% | | −22% | | −5% | |

| | $U_r/U_e$ | | | | $U_v/U_e$ | | | |
|---|---|---|---|---|---|---|---|---|
| | Mid-Baseline | | Final-Baseline | | Mid-Baseline | | Final-Baseline | |
| | Control | Treated | Control | Treated | Control | Treated | Control | Treated |
| Average | 0.004 | 0.034 | 0.042 | 0.027 | 0.017 | 0.063 | 0.092 | 0.048 |
| Standard Deviation | 0.105 | 0.064 | 0.062 | 0.064 | 0.073 | 0.078 | 0.132 | 0.073 |
| p value | p <0.21 | | p <0.45 | | p <0.08 | | p <0.13 | |
| % Difference from Baseline | 2% | 7% | 9% | 6% | 8% | 19% | 28% | 16% |
| Total % Difference (T − C) | 5% | | −3% | | 12% | | −12% | |

| | $U_r/U_f$ | | | |
|---|---|---|---|---|
| | Mid-Baseline | | Final-Baseline | |
| | Control | Treated | Control | Treated |
| Average | 0.024 | 0.014 | 0.012 | 0.003 |
| Standard Deviation | 0.034 | 0.040 | 0.036 | 0.037 |
| p value | p <0.47 | | p <0.46 | |
| % Difference from Baseline | 6% | 4% | 3% | 1% |
| Total % Difference (T − C) | −2% | | −2% | |

T = Treated
C = Control

Example 7

Corneometer

The general appearance of soft, smooth skin depends largely on the presence of an adequate amount of water in the stratum corneum. The Corneometer is a commercially available instrument (Courage & Khazaka, Germany) to measure the changes in capacitance of the skin resulting from changes in the degree of hydration. It is particularly sensitive to low levels of hydration, and uses measurements of arbitrary units of skin hydration (H) to express capacitance.

Tests were conducted using a Corneometer on both sides of the face on the cheek area. Changes in moisture content of the statum corneum occur rapidly due to changes in the environment, including hydration from the use of moisturizing agents and humectants. Thus, the measurements with the Ballistometer and Cutometer indicate changes occurred in deeper layers of the skin, rather than the superficial stratum corneum. Table IV shows no significant changes in the hydration of the stratum corneum following 2 weeks (p<0.84) and 5 weeks (p<0.67) of product use.

TABLE IV

Corneometer Readings

| | Skin Hydration (H) | | | |
|---|---|---|---|---|
| | Mid-Baseline | | Final-Baseline | |
| | Control | Treated | Control | Treated |
| Average | −5 | −7 | −8 | −4 |
| Standard Deviation | 6 | 7 | 5 | 7 |
| p value | p < 0.84 | | p < 0.67 | |
| % Difference from Baseline | −7% | −10% | −12% | −6% |
| Total % Difference (T-C) | −3% | | 6% | |

T = Treated
C = Control

Various modifications of the invention in addition to those shown and described herein will be apparent to those skilled in the art from the foregoing description. Such modifications are also intended to fall within the scope of the appended claims. The foregoing disclosure includes all the information deemed essential to enable those skilled in the art to practice the claimed invention.

What is claimed is:

1. An orally administered pharmaceutical composition for the prevention and treatment of skin conditions in a patient comprising:
   a sugar compound that is converted to a glycosaminoglycan in the patient in an amount sufficient to thicken the skin;

a primary antioxidant component in an amount sufficient to substantially inhibit the activity of collagenase and elastase;

at least one amino acid component in an amount sufficient to assist in the thickening of the skin; and at least one transition metal component in an amount effective to bind collagen and elastic fibers and thicken skin.

2. The pharmaceutical composition of claim 1, wherein the sugar compound is present in about 5 to 50 weight percent, the primary antioxidant component is present in about 5 to 50 weight percent, the amino acid component is present in about 8 to 60 weight percent, and the transition metal component is present in about 0.5 to 15 weight percent of the composition.

3. The pharmaceutical composition of claim 1, wherein the sugar compound comprises an N-acetylglucosamine compound or salt or ester thereof, the primary antioxidant component comprises ascorbic acid compound or salt or ester thereof, at least two amino acids selected from the group consisting of proline, lysine, cysteine, and methionine are present, and at least two the transition metal components comprising zinc, manganese or copper, or mixtures thereof, are present.

4. The pharmaceutical composition of claim 3, wherein at least three transition metal components are present, one of Which is zinc monomethionine, one of which is manganese ascorbate, and one of which is copper sebacate, wherein the zinc is present in about 10 to 30 weight percent of the complex and the manganese is present in about 5 to 20 weight percent of the complex, and the copper is present in about 5 to 20 weight percent of the complex.

5. The pharmaceutical composition of claim 3, wherein the N-acetylglucosamine is present in about 5 to 30 weight percent, the ascorbic acid is present in about 5 to 50 weight percent, the amino acid component comprises lysine and proline, wherein each is present in about 4 to 25 weight percent, and the zinc monomethionine and the manganese ascorbate are each present in about 1 to 10 weight percent and the copper sebacate is present in about 0.1 to 5 weight percent of the composition.

6. The pharmaceutical composition of claim 1, wherein the composition further comprises a pharmaceutically acceptable carrier or excipient.

7. The pharmaceutical composition of claim 1, further comprising a vitamin E source, a cysteine source, a vitamin $B_3$ source, quercetin dihydrate, pyridoxal 5 phosphate-Co $B_6$, a methionine source, and a vitamin A source.

8. The pharmaceutical composition of claim 7, wherein the vitamin E is D-alpha tocopheryl acid succinate present in about 1 to 15 weight percent, the vitamin $B_3$ is niacinamide present in about 0.5 to 15 weight percent, the vitamin A is vitamin A palmitate present in about 0.1 to 5 weight percent, the cysteine is N-acetyl cysteine present in about 1 to 10 weight percent, the methionine is preferably L-selenomethionine present in about 0.1 to 5 weight percent, the quercetin dihydrate is present in about 0.5 to 15 weight percent, and the pyridoxal 5 phosphate-Co $B_6$ is present in about 0.1 to 5 weight percent of the composition.

9. A method for the prevention or treatment of skin conditions, wherein the skin has a thickness of dermis and collagen, which comprises administering to a patient:

a sugar compound that is converted to a glycosaminoglycan in the patient in an amount sufficient to thicken the skin;

a primary antioxidant component in an amount sufficient to substantially inhibit the activity of collagenase and elastase;

at least one amino acid component in an amount sufficient to assist in the thickening of the skin; and at least one transition metal component in an amount effective to bind collagen and elastic fibers and thicken skin, so as to modify the thickness of the skin to prevent or treat at least one skin condition.

10. The method of claim 9, wherein the skin condition prevented or treated is at least one of wrinkles or the appearance thereof, fine lines or the appearance thereof, thinning, reduced skin elasticity, reduced skin moisture, spider veins, senile purpura, sun damaged skin, aging skin or rough skin.

11. The method of claim 9, wherein the sugar, the primary antioxidant, the at least one amino acid component, and the at least one transition metal component are administered simultaneously as a pharmaceutical composition.

12. The method of claim 11, wherein the composition is administered in conjunction with concurrent or subsequent treatment by at least one additional pharmaceutical composition for the prevention or treatment of a skin condition.

13. A method for the prevention or treatment of skin conditions, wherein the skin has a thickness of dermis and collagen, which comprises administering to a patient:

a sugar compound that is converted to a glycosaminoglycan in the patient in an amount sufficient to thicken the skin;

a primary antioxidant component in an amount sufficient to substantially inhibit the activity of collagenase and elastase;

at least one amino acid component in an amount sufficient to assist in the thickening of the skin;

at least one transition metal component in an amount effective to bind collagen and elastic fibers and thicken skin; and a catechin-based component present in an amount sufficient to inhibit the presence of an anti-collagen enzyme in the skin, so as to modify the thickness of the skin to prevent or treat at least one skin condition.

14. An pharmaceutical composition for the prevention and treatment of skin conditions in a patient consisting essentially of:

a sugar compound that is converted to a glycosaminoglycan in the patient in an amount sufficient to thicken the skin;

a primary antioxidant component in an amount sufficient to substantially inhibit the activity of collagenase and elastase;

at least one amino acid component in an amount sufficient to assist in the thickening of the skin; and at least one transition metal component in an amount effective to bind collagen and elastic fibers and thicken skin.

* * * * *